United States Patent
Schmidt et al.

(12)

(10) Patent No.: US 6,670,120 B1
(45) Date of Patent: Dec. 30, 2003

(54) CATEGORISING NUCLEIC ACID

(75) Inventors: Günter Schmidt, Houghton (GB); Andrew Hugin Thompson, Ayr (GB)

(73) Assignee: Xzillion GmbH & Co., Frankfurt am Main (DE)

( * ) Notice: Subject to any disclaimer, the term of this patent is extended or adjusted under 35 U.S.C. 154(b) by 0 days.

(21) Appl. No.: 09/462,635

(22) PCT Filed: Jul. 13, 1998

(86) PCT No.: PCT/GB98/02043

§ 371 (c)(1),
(2), (4) Date: Apr. 10, 2000

(87) PCT Pub. No.: WO99/02725

PCT Pub. Date: Jan. 21, 1999

(30) Foreign Application Priority Data

| | | |
|---|---|---|
| Jul. 11, 1997 | (GB) | 9714716 |
| Sep. 10, 1997 | (GB) | 9719284 |
| Dec. 19, 1997 | (GB) | 9726949 |

(51) Int. Cl.$^7$ .......................... C12Q 1/68; C07H 21/04
(52) U.S. Cl. ..................... 435/6; 435/91.1; 435/91.2; 536/23.1; 536/24.33
(58) Field of Search ................ 435/6, 91.1, 91.2; 536/23.1, 24.33

(56) References Cited

U.S. PATENT DOCUMENTS

| | | | | |
|---|---|---|---|---|
| 5,106,727 A | * | 4/1992 | Hartley et al. ................. | 435/6 |
| 5,508,169 A | * | 4/1996 | Deugau et al. ................. | 435/6 |
| 5,667,976 A | * | 9/1997 | Van Ness et al. .............. | 435/6 |
| 5,871,697 A | * | 2/1999 | Rothberg et al. .......... | 422/68.1 |
| 6,297,017 B1 | * | 10/2001 | Schmidt et al. ............... | 435/6 |

FOREIGN PATENT DOCUMENTS

| | | | | |
|---|---|---|---|---|
| EP | 0 370 694 | 5/1990 | | |
| EP | 0 735 144 A1 | * 3/1996 | ...................... | 1/68 |
| EP | 0 735 144 | 10/1996 | | |
| WO | WO 94/01582 | * 1/1994 | ...................... | 1/68 |

OTHER PUBLICATIONS

Dynal, Technical Handbook Second Edition, 1995, p. 116–119.*
Wong et al., Nucleic Acids Research, vol. 19, No. 9, May 11, 1991, pp 2251–2259, XP000204316.
Guilfoyle et al., Nucleic Acids Research, vol. 25, No. 9, May 1, 1997, pp. 1854–1858, XP 002076198.

* cited by examiner

*Primary Examiner*—Jeffrey Fredman
*Assistant Examiner*—Jeanine Goldberg
(74) *Attorney, Agent, or Firm*—Burns, Doane, Swecker & Mathis, L.L.P.

(57) ABSTRACT

The present invention involves a method for categorizing nucleic acid which comprises: producing a nucleic acid population by action of an endonuclease on double-stranded nucleic acid, such that each nucleic acid in the nucleic acid population has a double-stranded portion; contacting the nucleic acid population with one or more oligonucleotide sequences; and isolating nucleic acid which correctly hybridizes to an oligonucleotide sequence. In the method of the present invention, each oligonucleotide sequence has a pre-determined recognition sequence. Furthermore, the nucleic acid is categorized by its ability to correctly hybridize to oligonucleotide sequences having the recognition sequence, the recognition sequence being situated such that it recognizes a sequence in the double-stranded portion of the nucleic acid. The oligonucleotide sequence can comprise one or more different recognition sequences.

17 Claims, 5 Drawing Sheets

CATEGORISING NUCLEIC ACID

The present invention concerns a method for categorising nucleic acid. In particular, the invention concerns a method for sorting nucleic acid, which method permits reduction in the complexity of a nucleic acid population of approximately one order of magnitude, or more. The invention also relates to a kit for carrying out the above method.

Analysis of nucleic acids is fundamental to much of modem molecular biology. A particular feature of nucleic acids derived from living organism is that they are almost invariably complex populations of sequences present in widely varying quantities. In order to characterise these populations of nucleic acids it is usual to attempt to reduce the complexity of the population of nucleic acids in some way. Traditionally the approach has been to clone complex nucleic acid molecules into vectors to allow them to be isolated and either sub-cloned further or analysed directly. Cloning requires the use of biological hosts and these are often difficult to use and require a great deal of specialist knowledge for the cloning procedures to be successful. The traditional processes of cloning to generate libraries of sequences are also only partially automatable.

A problem which cloning does not address is how to isolate sequences which are present only at low copies in backgrounds of sequences present at high copy numbers. Various techniques have been developed to 'normalise' complex nucleic acid populations prior to cloning in order to increase the quantities of sequences at low copy numbers relative to those at high copy numbers. Subtractive hybridisation methods have been used to try and normalise cDNA populations.

PCT/GB93/01452 describes methods of molecular sorting which uses restriction endonucleases that generate ambiguous sticky-ends in the nucleic acid sanple to be sorted. Adapters are designed with sticky ends complementary to a single sticky-end sequence or a subset of the these ambiguous sticky ends such that the individual sticky end or subset thereof is coupled to a distinct sequence in the double stranded region of the adapter. This allows subsets of the adaptored nucleic acid to be amplified using specific primers corresponding to sequences within the adapter which in turn relate to the sequence of the sticky end of the adapter. U.S. Pat. No. 5,508,169 (issued Nov. 7, 1995) describes methods very similar to those disclosed in PCT/GB93/01452.

A problem with the above method is that the nucleic acids can be sorted only according to the sequence present on the sticky-ends of the nucleic acid. The sticky-end sequence is of limited length, as determined by the choice of restriction enzyme, thus the basis for sorting is limited.

It is an object of the present invention to provide a method which overcomes the above problems, and provides a wider basis on which sorting of nucleic acid populations can be carried out, not limited by the sticky-end sequence. It is also an object of this invention to provide methods to reduce the complexity of nucleic acid populations by allowing them to be sorted into sub-populations without cloning and to permit normalisation of these populations. This invention describes methods of sorting nucleic acid molecules that have a variety of applications including gene expression profiling, preparation of templates for sequencing, linkage analysis, etc. This invention provides methods of generating sorted libraries. In many applications it is preferable that these sorted nucleic acids be captured on a solid phase support.

Accordingly, the present invention provides a method for categorising nucleic acid, which method comprises producing a nucleic acid population by action of an endonuclease on double-stranded nucleic acid, such that each nucleic acid in the nucleic acid population has a double-stranded portion, contacting the nucleic acid population with one or more oligonucleotide sequences, and isolating nucleic acid which correctly hybridises to an oligonucleotide sequence, wherein each oligonucleotide sequence has a pre-determined recognition sequence, the nucleic acid being categorised by its ability to correctly hybridise to oligonucleotide sequences having the recognition sequence, the recognition sequence being situated such that it recognises a sequence in the double-stranded portion of the nucleic acid, one or more different recognition sequences being represented in the oligonucleotide sequences.

The present invention also provides kit for categorising a nucleic acid, comprising one or more adaptors and one or more sets of oligonucleotide sequences, wherein the adaptors comprise nucleic acid having a double-stranded primer portion of a known sequence and a single-stranded portion of a pre-determined length, either each single-stranded portion of each nucleic acid in the adaptors having the same pre-determined sequence or all possible sequences of the single-stranded portion being represented in the adaptors, and wherein each oligonucleotide sequence comprises a first sequence, a second sequence attached to the first sequence and a third sequence attached to the second sequence, in which the first sequence is complementary to the sequence of the primer portion of the adaptor, the second sequence is the same sequence as the single-stranded portion of the adaptors or all possible second sequences of the same length as the single-stranded portion of the adaptors are represented within the set of oligonucleotides, and the third sequence comprises a pre-determined recognition sequence.

The invention will now be described in further detail by way of example only, with reference to the accompanying drawings, in which.

Figure 1:
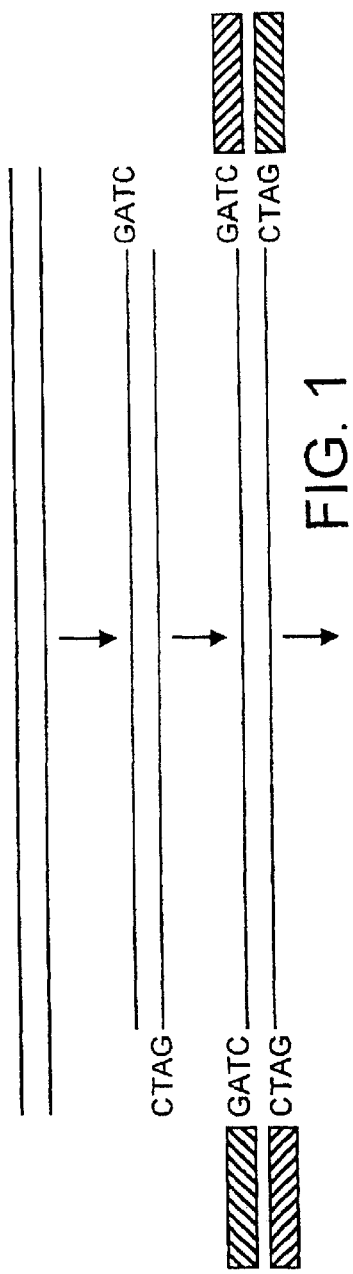
FIG. 1 shows a schematic of the treatment of a genomic DNA clone with a frequent cutting restriction endonuclease, such as Sau3A1, followed by ligation of adaptors to restriction fragments bearing specific primer sequences—all fragments are dealt with simultaneously, but for simplicity only one is shown.
Figure 2:
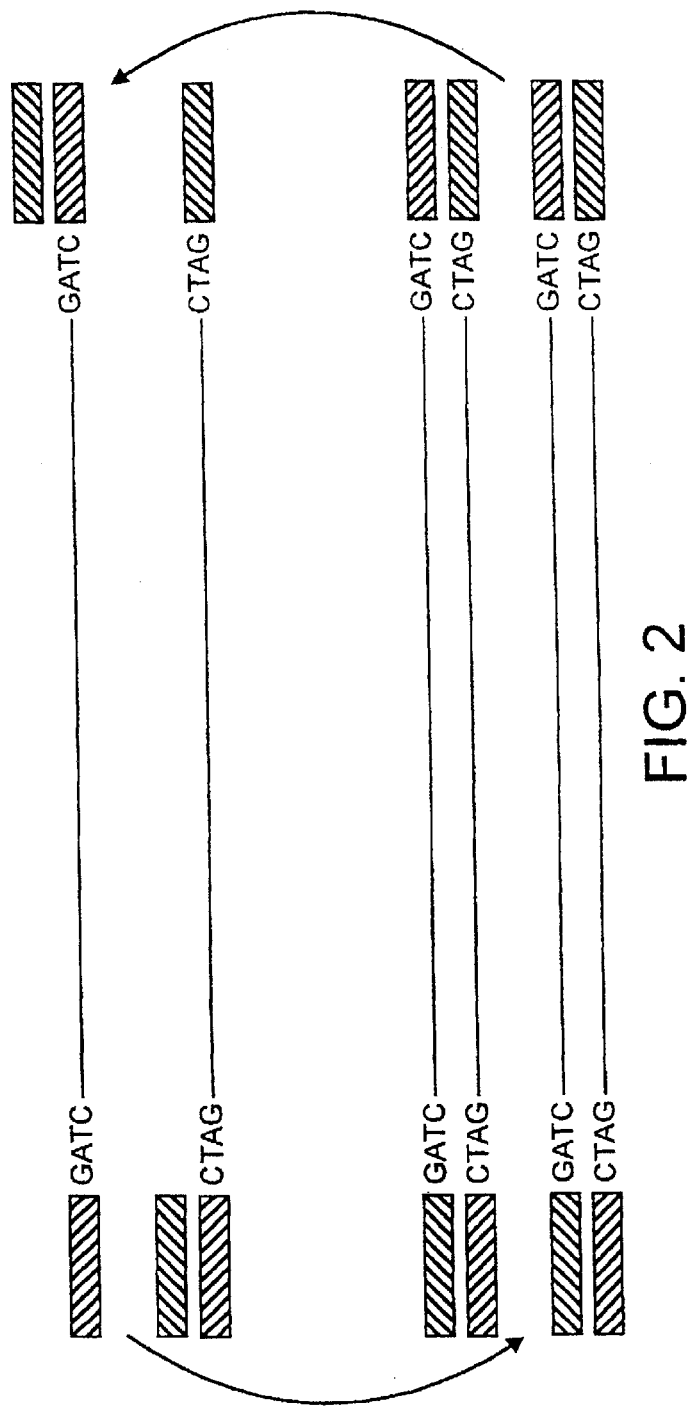
FIG. 2 shows a schematic of an amplification step, following the steps of FIG. 1, in which fragments are amplified by PCR using adaptor primers.
Figure 3:
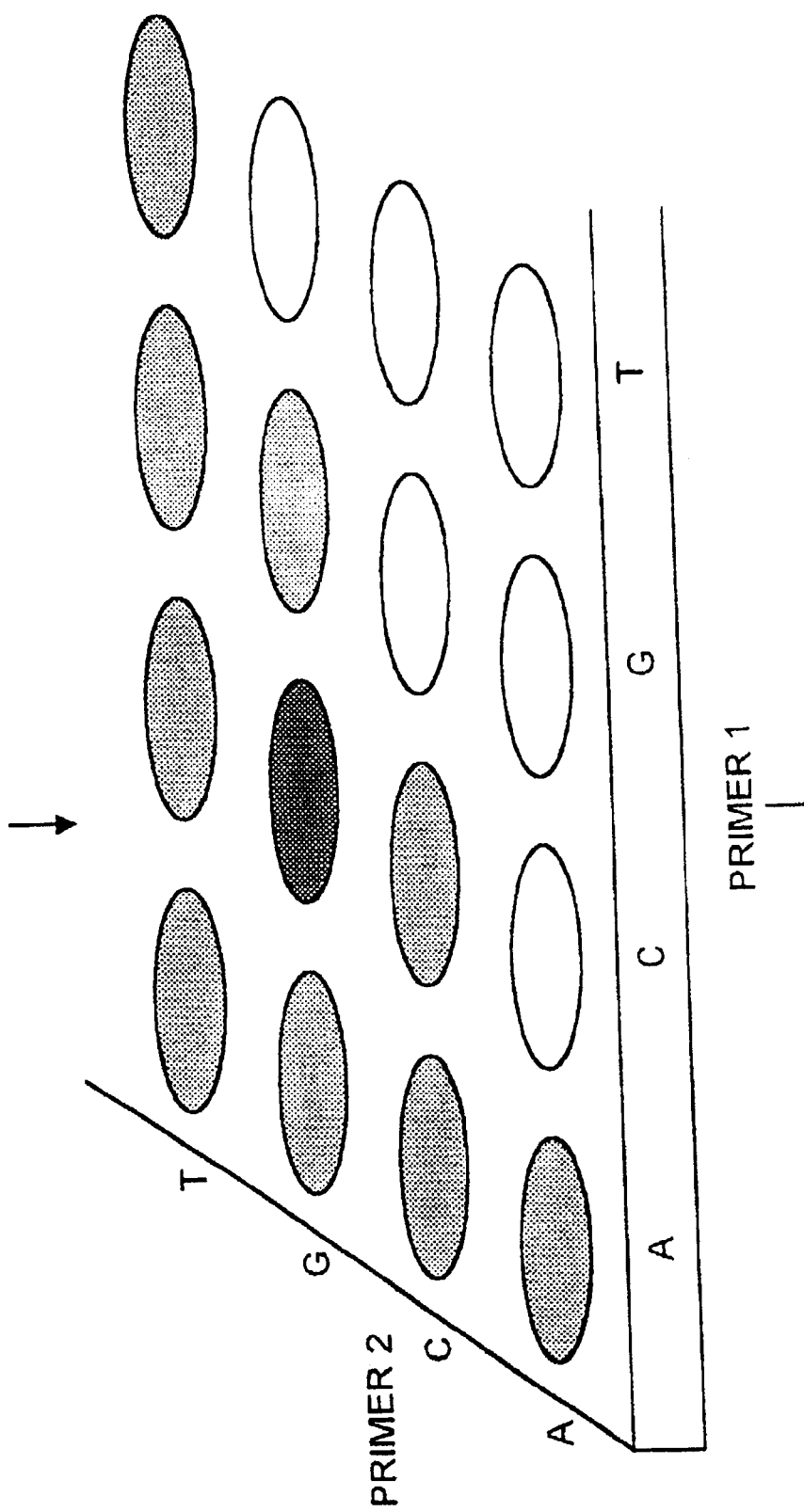
Figure 4:
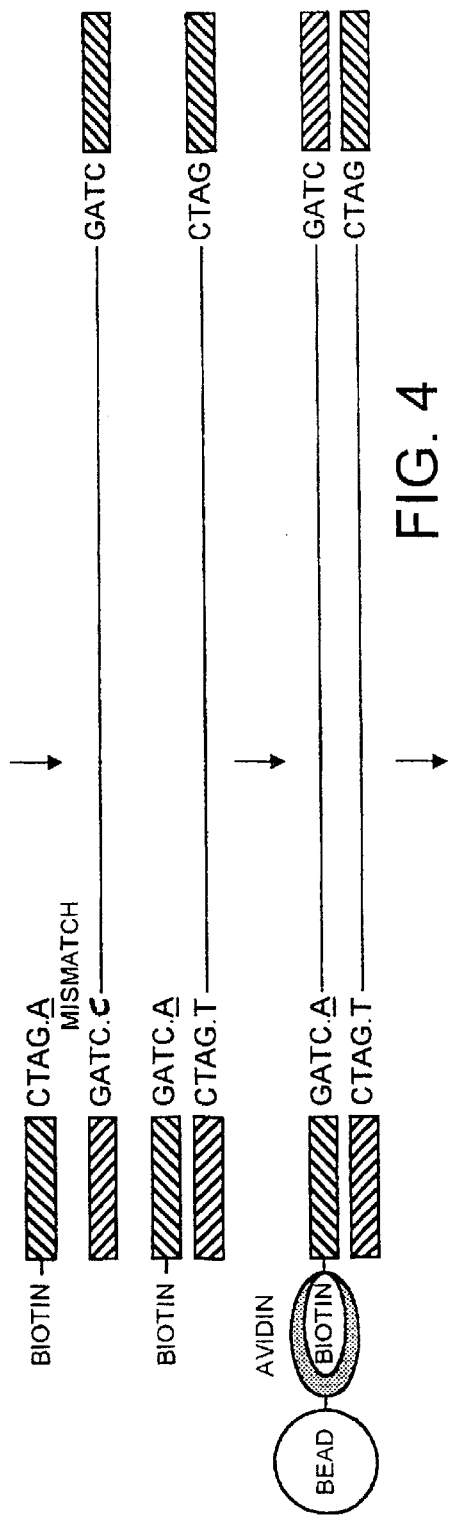
Figure 5:
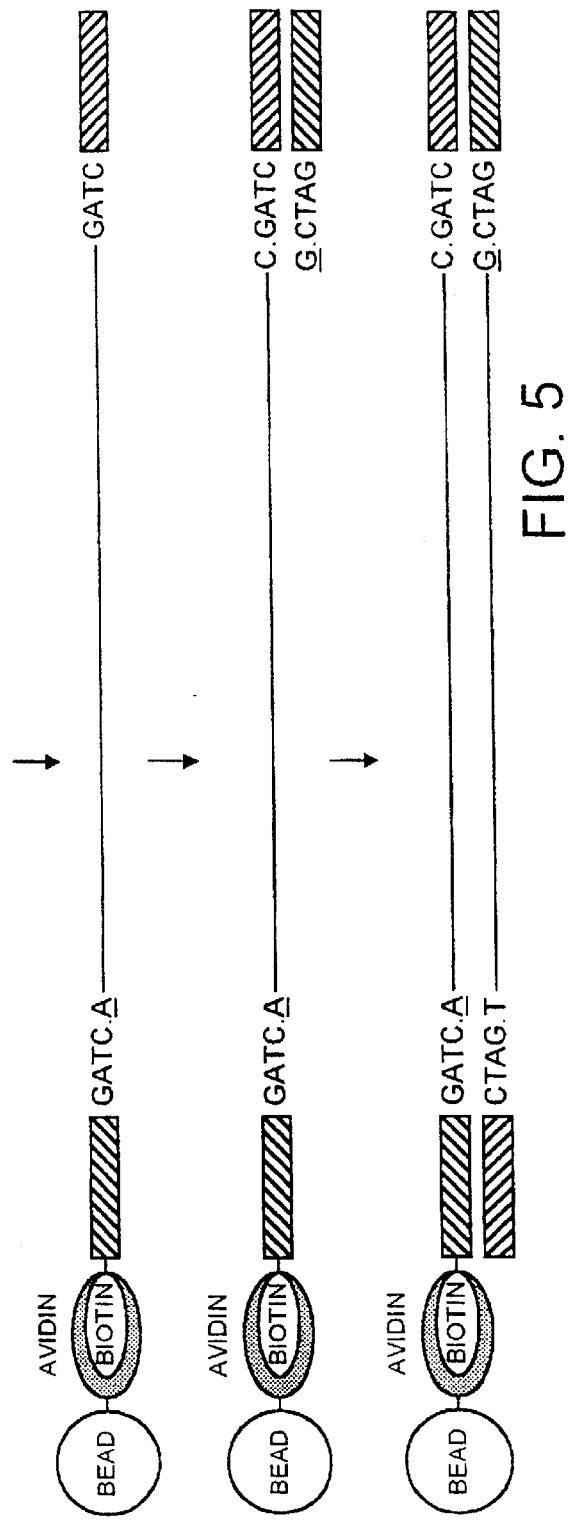
Figure 6A:
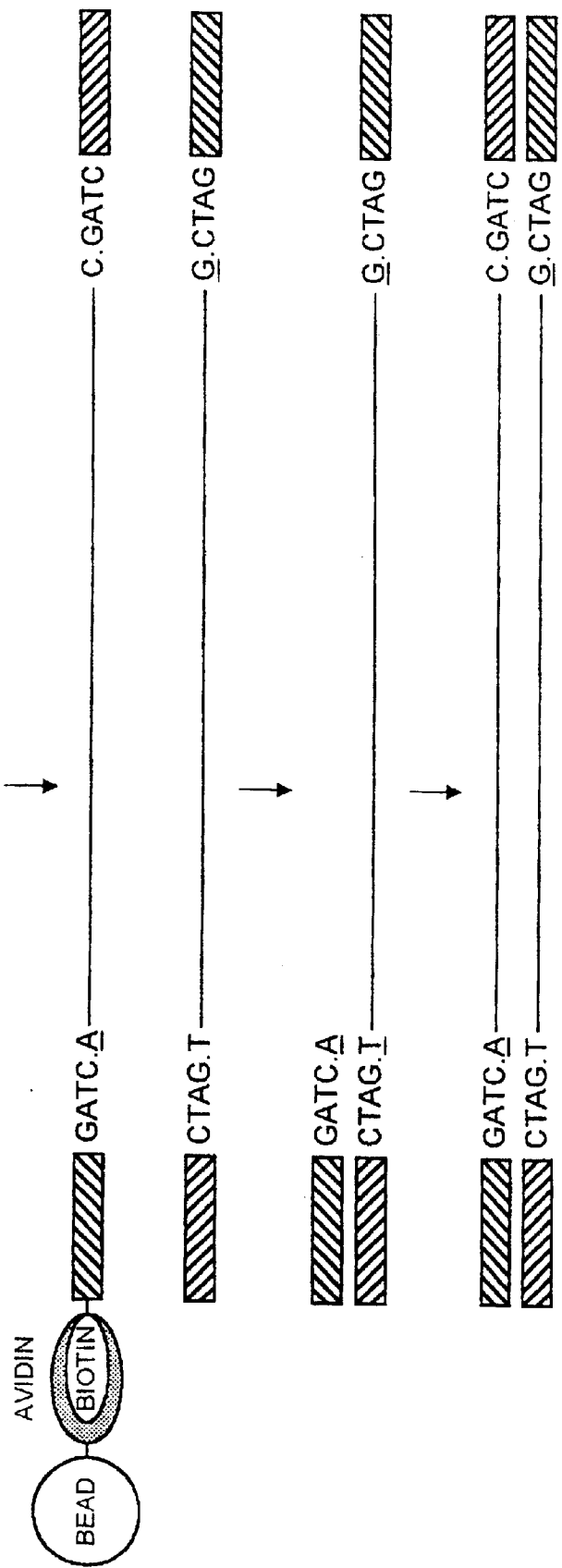
Figure 6B:
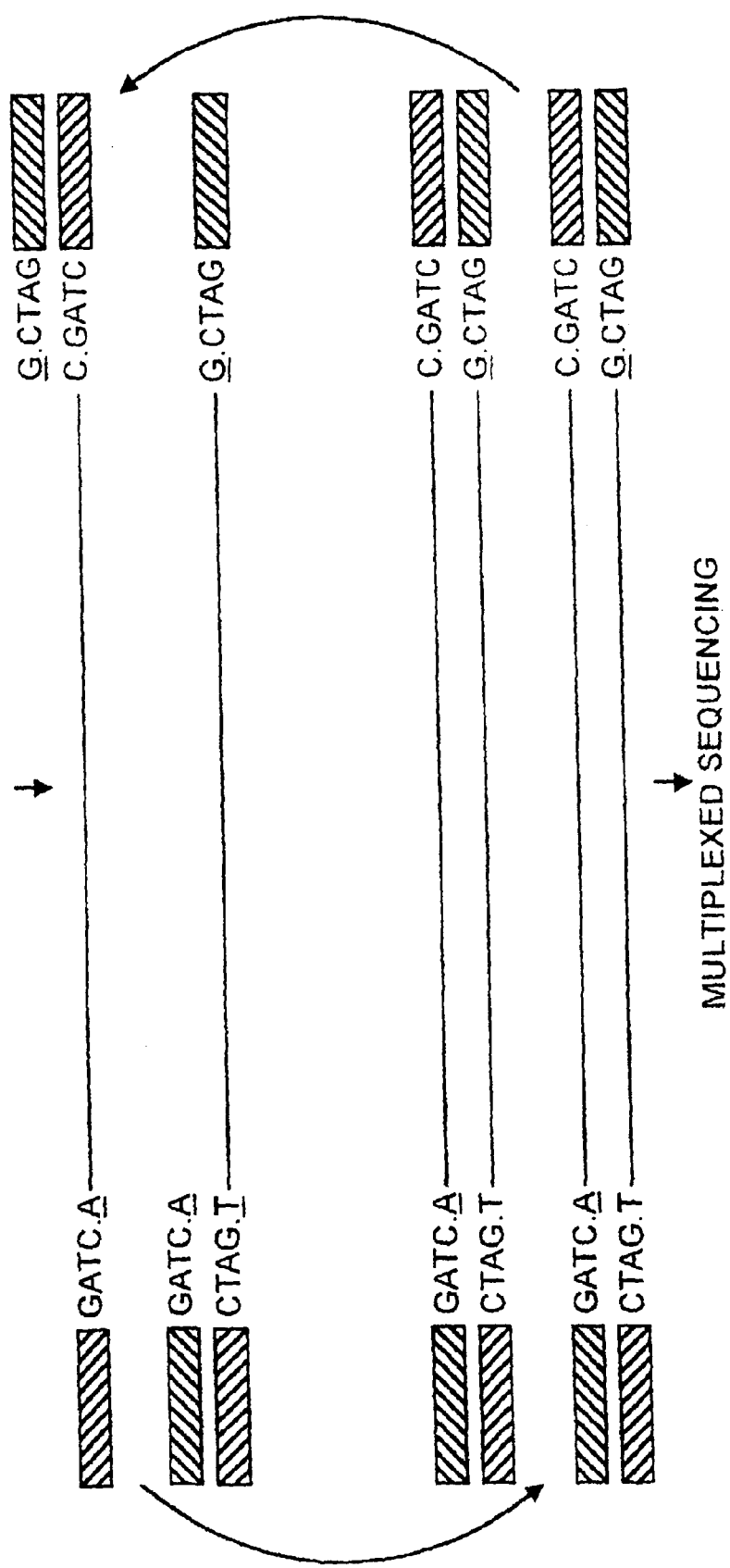

FIG. 3 shows a step following the step of FIG. 2, in which amplified fragments are subdivided into 10, wells, each well being identified by a pair of primers used to sort added molecules, each well initially containing one of the pair of primers, there being 4 primers each with one base probe sequence and each well having 1 of 10 possible pairs generated by a combination of the four primers, the second primer being added after one cycle of synthesis of the first;

FIG. 4 shows a schematic of a differential amplification step, following the step of FIG. 3, in which the contents of a well containing a primer terminated with AC followed by a probe terminated by AG is amplified and then one cycle of synthesis is performed with the first primer and double strands captured with avidinated beads;

FIG. 5 shows a schematic of steps subsequent to those of FIG. 4, in which the non-immobilised strand is melted off and washed away and the reaction residue polymerised, a second primer then being added and a second cycle of synthesis performed; and FIGS. 6A and 6B show a schematic of steps subsequent to those of FIG. 5, in which the non-immobilised strand is melted off and transferred to a fresh reaction vessel, and both primers are then added to the fresh free strand to amplify by PCR.

In the present invention, the nucleic acid population is not isolated (such as by capture onto a solid phase) prior to contacting it with the oligonucleotide sequence(s). Thus each nucleic acid in the population may initially move freely in the suspension or solution in which it is contained. After contacting the nucleic acid population with the oligonucleotide sequence(s), preferably only the nucleic acid(s) which have correctly hybridised to the oligonucleotide sequence(s) are isolated (preferably by capture onto a solid phase).

In more detail, the method of this invention may comprise the following steps:

1. Restricting a large nucleic acid or population of large nucleic acids to generate fragments with known termini.

2. Ligating adaptors or linkers to the termini of these nucleic acid molecules. The ligated adaptor provides a known sequence at the termnini of a population of nucleic acids which can be used to design primers which extend beyond the terminal adaptor sequence into unknown sequence adjacent to the known adaptor sequence allowing the unknown sequence to be probed.

3. Optionally amplifying the adaptored fragments using primers complementary to the whole or part of the adaptor sequences at the termini of the adaptored fragments.

4. Optionally normalising the population of adaptored nucleic acids.

5. Selectively amplifying subsets of the nucleic acids through the use of pairs of primers which partially overlap into the unknown sequence. The overlapping primer will hybridise to a subset of the whole population. The size of the subset is determined by the length of overlap of the primer into the adjacent sequence.

The methods of this invention may be applied cyclically to sub-populations of sorted nucleic acids generated by the methods of this invention. Each cycle further reduces the complexity of the population. If necessary the cycles can be repeated until unique nucleic acid is obtained.

In a preferred embodiment the step of restricting nucleic acid is coupled to the ligation of adapters. Preferred restriction endonucleases for use with this invention cleave within their recognition sequence generating sticky-ends that do not encompass the whole recognition sequence. This allows adapters to be designed that bear sticky ends complementary to those generated by the preferred restriction endonuclease but which do not regenerate the recognition site of the preferred restriction endonuclease. This means that if the restriction reaction is performed in the presence of ligase and adapters, the ligation of restriction fragments to each other is reduced by continuous cleavage of these ligations whereas ligation of adapters is irreversible so the presence of adapters drives the restriction to completion and similarly the restriction endonuclease drives the ligation reaction to completion. This process ensures that a very high proportion of restriction fragments are ligated to adaptors. This is advantageous as ligation of adapters to restriction fragments is a relatively inefficient process. This is due to random ligation of restriction products to each other if these are phosphorylated. In this embodiment the adapters used are preferably not phosphorylated at their 5' hydroxyl groups so that they cannot ligate to themselves. GB 9115407.0 describes a method of normalising a population of nucleic acids comprising the following steps:

1. Combining a mixture of heterogeneous DNA fragments with oligonucleotide primers compatible with some nucleic acid amplification system and denaturing the double stranded heterogeneous DNA.

2. Altering the conditions, i.e. reducing the temperature, to allow the more common species to re-anneal while preventing the primers from annealing to the DNA. The temperature for re-annealing at this stage must be higher than the melting temperature of the PCR primers.

3. Altering the reaction conditions further to allow the PCR primers to anneal to the remaining single stranded DNA which should represent the rarer species.

4. Performing strand extension of the primed species.

Advantageously, the above steps are applied cyclically a number of times to amplify the rarer species to a significant extent.

Application of this method to sequences with known termini permits the design of primers with very specific melting temperatures allowing the method to be used generically. Use of this method is particularly advantageous in reducing the complexity of genomic DNA as a significant proportion of most genomic DNA is repetitive sequence.

The advantage of providing a known sequence adjacent to probe sequence allows one to design libraries of probes, where all the probes in a library have the same melting temperature. This is advantageous as hybridisation of the entire library can be performed simultaneously at a single temperature whilst retaining the stringency of hybridisation.

Consider a large DNA fragment such as a mitochondrial genome or a cosmid or a microbial genome. To perform steps 1 to 4 of the method described above, such a large molecule can be cleaved with a frequently cutting restriction enzyme to generate fragments of the order of a few hundred bases in length. If a restriction endonuclease like Sau3A1 is used fragments with a known sticky end are left, to which double stranded adaptors can be ligated. These adaptors will bear a known primer sequence, and a sticky end complementary to that produced by the restriction endonuclease to permit ligation. A combined restriction and ligation protocol as described above is appropriate.

The majority of properly restricted fragments as a result bear an adaptor at each of their termini. This permits amplification of the adaptored restriction fragments at this stage if that is desired. After adaptoring and any non-selective amplification and normalisation, the nucleic acids can be differentially amplified to generate specific subsets of the starting population. The method of differential amplification preferably comprises the following steps:

1. Dividing the adaptored population of restriction fragments into separate wells. If, for example, primers with an overlap of a single base are used then the adaptored fragments would be divided into 10 or 16 wells.

2. Adding to each well one type of biotinylated primer of a predetermined set. The primer bears a sequence complementary to that provided by the adaptor and restriction site. The primer additionally bears an overlap of a predetermined number of bases beyond the known sequence into the unknown sequence immediately adjacent to the restriction site. Primers with different overlaps are added to different well. Four primers are need if a 1 base overlap is used. If 16 wells are used each of the 4 primers are added to 4 wells.

3. Denaturing the amplified fragment population that was subdivided into each well by raising the temperature. The temperature is then reduced to permit the primer sequences to anneal. Primers preferably have equalised melting temperatures so that conditions for use of all primers are the same.

4. Adding thermostable polymerase and nucleotides to extend annealed primers.

5. Capturing the biotinylated strand extension products from (4) onto a solid phase substrate derivitised with avidin. This may be effected through the addition of avidinated beads. These may optionally be magnetic beads.

6. Melting off the non-biotinylated complementary strand and washing this away. This leaves a single stranded copy of the selected fragments immobilised on the solid phase support.

7. To each of the separate pools is added one of the same set of primers as used in step (2) but not biotinylated, such that each pool receives a different combination of primers from this step and step (2). The primers should anneal to the single stranded capture molecules from (6). If 16 pools are used, to each is added one of the same 4 primers, but not biotinylated such that each of the 16 pools carries one of the possible different combinations of pairs of the 4 primers.

8. Extending the primed captured strands with polymerase and nucleotide triphosphates.

9. Denaturing the free strand from the captured strand by raising the temperature. The 'selected' free strand is thus released into solution. The liquid phase can be transferred to fresh reaction vessel or the solid phase support bearing the captured strands from (5) can be removed. This is very easy if the support used are magnetic beads as these can be removed by electromagnetic attraction to a probe.

The isolated free strands from (9) are thus isolated. At this stage the selected strands can be captured onto a solid phase support or amplified or the process of differential amplification can be repeated on the isolated subsets generated to further sub-sort these populations. This would be effected by using primers which overlap further into the unknown sequence adjacent to the known sequence of the adapter and the selected fragment. The sorted fragment could equally be cloned into a biological vector at this stage if desired.

Generating a captured library is advantageous in that it facilitates easy manipulation of the library of fragments. Such manipulations include copying, amplification and probing of the library for particular sequences. A captured library dispenses with any requirement for biological cloning vectors to maintain the library as such a library can be readily copied using polymerases and nucleotide triphosphates. The captured library can be readily washed and can very easily be stored in a refrigerated environment.

It should be noted in the example of primers that overlap by a single base, that the amplification products from the well containing a primer terminated by A followed by the primer terminated by G gives the complement of the well where G is followed by A. It might therefore be desirable to pool the reactions of where the same pair of primers are present but used in a different order to ensure that both strands of each DNA molecule are present and captured on the solid phase support. This would thus give 10 different pools. This is a convenient number as one can reduce the complexity of a library by one order of magnitude with four primers. Each sorted library of fragments can be further sub-sorted to an arbitrary degree.

An alternative embodiment of this method uses primers already immobilised on a solid phase support, preferably covalently linked to the support instead of biotinylated primers in step (2) of the differential amplification process. Such solid phase supports can be magnetic beads, as described in EP-A-0 091 453 and EP-A-0 106 873, or the support could be polymer beads. PCT/GB92/02394 describes a solid phase polymer support in a micro-column where the solid phase support are beads of silica gel. The beads are retained between two frits in the column through which solvents and reagents can flow. Such apparatus is also applicable with this invention.

One can clearly repeat the sorting process starting from a captured library that has been previously sorted.

One can also clearly use just 10 wells to generate sorted populations as all of the sequence information in a series of 16 wells will be present if just the 10 different pairs of primer combinations are used.

It should also be clear that labels can be introduced into sorted molecules by the primers used as part of the sorting process. Methods of introducing labels into primer oligonucleotides are well known in the art. Biotin has been discussed above, but many others are applicable.

One can also use probes which overlap beyond the provided adaptor sequence to any extent. It becomes more difficult, however, to ensure the stringency of hybridisation as the number of bases extending into the unknown sequence from the adaptor is increased.

To effect higher degrees of sorting one can either sort a sorted library with a set of four primers that overlap beyond the known terminal sequences by a single base or one can use primers with a longer sequence overlap. To sort an adaptored population of nucleic acid fragments using primers with a 2 base overlap beyond the adaptor sequence, the adaptored population of restriction fragments is sub-divided into 256 wells. In each well is one of 16 biotinylated primers which bear a sequence complementary to that provided by the adaptor and restriction site. The primers additionally bear an overlap of 2 bases beyond the known sequence into the unknown sequence immediately adjacent to the restriction site. The amplified fragment population subdivided into each well is denatured by raising the temperature and cooled allowing the primer sequences to anneal. Primers, again, preferably have equalised melting temperatures so that conditions for use of all primers is the same. Thermostable polymerase and nucleotides are added to extend annealed primers. Biotinylated fragments are captured onto a solid phase substrate via avidin and the complementary strand is melted off and washed away. To each of the 256 pools is added one of the same 16 primers, but not biotinylated such that each of the 256 pools carries one of the possible different combinations of pairs of the 16 primers. Again, AT followed by GC gives the complement of the reaction of GC followed by AT so it might be desirable to pool these pairs to give a total of 136 pools. For an overlap of n bases, one can distinguish $4^n$ distinct sequences. If both termini of a molecule are used to select fragments then one can distinguish fragments into $(4^n \times (4^n+1)/2)$ distinct sets, since the orientation of each fragment is unknown.

Sorting a library resolves fragments from a large, complex population into defined sets whose size will be statistically regular and determinable as long as the size of the parent library is known, even if only approximately. The composition of the sorted library will be less complex than that of the parent library. This allows for useful manipulations of a large library without loss of information as all the sequences present in the starting library should be present in one of the sub libraries as long as long as all of the possible sub-libraries are generated. This method offers greater ease of manipulation of complex nucleic acid libraries and greater precision of manipulation than cloning into biological vectors.

To put this invention into practise requires the construction of probe oligonucleotides (ONs). Precise control over hybridisation conditions will be required to ensure clean results in differential amplification.

Details and reviews on the construction of labelled and modified ONs are available in numerous up-to-date texts, see references 1 to 6 below. A brief discussion of preferred design possibilities is given below.

There are major differences between the stability of short oligonucleotide duplexes containing all Watson-Crick base pairs. For example, duplexes comprising only adenine and thymine are unstable relative to duplexes of guanine and cytosine only. These differences in stability can present problems when trying to hybridise mixtures of short oligonucleotides to a target RNA. Low temperatures are needed to hybridise A-T rich sequences but at these temperatures G-C rich sequences will hybridise to sequences that are not fully complementary. This means that some mismatches may occur, and specificity can be lost for the G-C rich sequences. At higher temperatures G-C rich sequences will hybridise specifically but A-T rich sequences will not hybridise.

It is desirable that probes within a library behave in a similar manner, i.e. they should have similar melting temperatures and preferably also binding kinetics. In order to normalise these effects, modifications can be made to nucleic acids. Modifications fall into three broad categories: base modifications, backbone modifications and sugar modifications.

Base Modifications

Numerous modifications can be made to the standard Watson-Crick bases. The following are examples of modifications that should normalise base pairing energies to some extent but they are not limiting:

The adenine analogue 2,6-diaminopurine forms three hydrogen bonds to thymine rather than two and therefore forms more stable base pairs.

The thymine analogue 5-propynyl dU forms more stable base pairs with adenine.

The guanine analogue hypoxanthine forms two hydrogen bonds with cytosine rather than three and therefore forms less stable base pairs.

These and other possible modifications should make it possible to compress the temperature range at which short oligonucleotides can hybridise specifically to their complementary sequences.

Backbone Modifications

Nucleotides may be readily modified in the phosphate moiety. Under certain conditions, such as low salt concentration, analogues such as methylphosphonates, triesters and phosphoramidates have been shown to increase duplex stability. Such modifications may also have increased nuclease resistance. Further phosphate modifications include phophodithirates and boranophosphates, each of which increase the stability of ONs.

Isosteric replacement of phosphorus by sulphur gives nuclease resistant ONs (reference 7). Replacement by carbon at either phosphorus or linking oxygen is also a further possibility.

Sugar Modifications

Various modifications to the 2' position in the sugar moiety may be made (references 12 and 13). The sugar may be replaced by a different sugar such as hexose or the entire sugar phosphate backbone can be entirely replaced by a novel structure such as in peptide nucleic acids (PNA). For a discussion see reference 8. PNA may be the ideal choice as it forms duplexes of the highest thermal stability of any analogues so far discovered.

Artificial Mismatches

One major source of error in hybridisation reactions is the stringency of hybridisation of the primers to the target sequence and to the unknown bases beyond. If the primers designed for a target bear single artificially introduced mismatches the discrimination of the system is much higher (Zhen Guo et al., Nature Biotechnology 15, 331–335, April 1997). Additional mismatches are not tolerated to the same extent that a single mismatch would be when a fully complementary primer is used. Thus this can be exploited in the method disclosed above. If the probe used to extends beyond the provided sequence by 1 base, an artificial mismatch, 1 helical turn away from the probe base destabilises the double helix to a considerable degree if there is a second mismatch at the probe site.

Details on effects of hybridisation conditions for nucleic acid probes can be found in references 9 to 11.

Mass labels for use in the present invention are disclosed in patent application PCT/GB98/00127. Further labels for use in the present invention are discussed in the UK applications of Page White & Farrer file numbers 87820, 87821, 87900.

References (1) Gait, M. J. editor, 'Oligonucleotide Synthesis: A Practical Approach', IRL Press. Oxford, 1990
(2) Eckstein. editor, 'Oligonucleotides and Analogues: A Practical Approach', IRL Press, Oxford, 1991
(3) Kricka, editor. 'Nonisotropic DNA Probe Techniques', Academic Press, San Diego, 1992
(4) Haugland, 'Handbook of Fluorescent Probes and Research Chemicals', Molecular Probes. Inc., Eugene, 1992
(5) Keller and Manack, 'DNA Probes. 2nd Edition', Stockton Press, New York, 1993
(6) Kessler, editor, 'Nonradioactive Labelling and Detection of Biomolecules', Springer-Verlag, Berlin, 1992.
(7) J. F. Milligan, M. D. Matteucci, J. C. Martin, J. Med. Chem. 36(14), 1923–1937,1993.
(8) P. E. Nielsen, Annu. Rev. Biophys. Biomol. Struct. 24, 167–183, 1995.
(9) Wetmur, Critical Reviews in Biochemistry and Molecular Biology, 26, 227–259, 1991
(10) Sambrook et al, 'Molecular Cloning: A Laboratory Manual, 2nd Edition', Cold Spring Harbour Laboratory, New York, 1989
(11) Hames, B. D., Higgins, S. J., 'Nucleic Acid Hybridisation: A Practical Approach', IRL Press, Oxford, 1988
(12) C. J. Guinosso, G. D. Hoke, S. M. Freier, J. F. Martin, D. J. Ecker, C. K. Mirabelle, S. T. Crooke, P. D. Cook, Nucleosides Nucleotides 10, 259–262, 1991.
(13) M. Carmo-Fonseca, R. Pepperkok, B. S. Sproat, W. Ansorge, M. S. Swanson, A. I. Lamond, EMBO J. 7, 1863–1873, 1991.

We claim:

1. A method for sorting nucleic acid, wherein said method comprises:
  (i) digesting double-stranded nucleic acid with an endonuclease to produce a nucleic acid population, wherein said endonuclease is selected such that each nucleic acid in the resulting nucleic acid population has a sticky end of a known base sequence and of a known common length extending from a terminal of its double-stranded portion, and wherein each nucleic acid in the nucleic acid population has a double-stranded portion;
  (ii) contacting the nucleic acid population with an adaptor to ligate the adaptor to a terminal of each nucleic acid in the nucleic acid population, wherein said adaptor comprises a double-stranded primer portion having a known base sequence, and a single-stranded portion complementary to the known sticky end of the nucleic acids in the nucleic acid population;

(iii) sorting the nucleic acid by isolating nucleic acids wherein both termini of the double-stranded portion of said nucleic acid correctly hybridize to an oligonucleotide sequence by contacting a first set of oligonucleotide sequences with the nucleic acid population by:

(a) denaturing the nucleic acid population in the presence of the first set of oligonucleotide sequences covalently linked to a solid phase support to produce a single-stranded nucleic acid population and allowing the single-stranded nucleic acid to hybridise to the first set of oligonucleotide sequences, wherein each oligonucleotide sequence in said first set of oligonucleotide sequences has a predetermined recognition sequence, the nucleic acid being categorized by its ability to correctly hybridize to oligonucleotide sequences having the recognition sequence, the recognition sequence being situated such that it recognizes a sequence in the portion of the nucleic acid which was double-stranded after digestion with the endonuclease;

(b) immobilizing those nucleic acids which correctly hybridise to the oligonucleotide sequence added to that well;

(c) extending the correctly hybridised oligonucleotide sequences along the single-stranded portion of the immobilised nucleic acid to form double-stranded nucleic acid;

(d) denaturing the double-stranded nucleic acid and removing non-immobilised species to isolate the resulting immobilised single-stranded nucleic acid;

(e) contacting the immobilised single-stranded nucleic acid with a second set of oligonucleotide sequences, wherein each oligonucleotide sequence in said second set of oligonucleotide sequences has a predetermined recognition sequence, the nucleic acid being categorized by its ability to correctly hybridize to oligonucleotide sequences having the recognition sequence, the recognition sequence being situated such that it recognize a sequence in the portion of the nucleic acid which was double-stranded after digestion with the endonuctease;

(f) extending the correctly hybridised oligonucleotide sequences along the immobilised single-stranded nucleic acid to form double-stranded nucleic acid;

(g) denaturing the double-stranded nucleic acid; and (h) isolating the resulting non-immobilised single-stranded nucleic acid; and (iv) further sorting the isolated single stranded nucleic acid of step (h) by repeating step (iii) on the isolated single stranded nucleic acid of step (h), wherein the first set of oligonucleotide sequences is replaced by a third set of oligonucleotide sequences, each oligonucleotide sequence of the third set recognizing a further portion of the nucleic acid which was double stranded after digestion with the endonuclease, and wherein the second set of oligonucleotide sequences is replaced by a fourth set of oligonucleotide sequences, each oligonucleotide sequence of the fourth set recognizing a further portion of the nucleic acid which was double stranded after digestion with the endonuclease.

2. The method according to claim 1, wherein the extended and isolated products of the first step and/or the extended and isolated products of the second step are amplified by PCR.

3. The method according to claim 1, wherein the correctly hybridised nucleic acids are immobilised by immobilising the oligonucleotide sequences.

4. The method according to claim 3, wherein each oligonucleotide in the first set of sequences carries a biotin residue such that prior to or after hybridising to the nucleic acid the sequence is captured on an avidinated solid phase.

5. The method according to claim 3, wherein each oligonucleotide in the first set of sequences is covalently attached to a solid support prior to contacting with the nucleic acid population.

6. The method according to claim 1, wherein the recognition sequence of the first and second set of oligomleteotide sequences consists of one base and, prior to performing the first step, the nucleic acid population is sub-divided into 16 wells, each well containing oligonucleotides from the first set of sequences having one of the four possible recognition sequences and wherein in the second step oligonucleotides from the second set of sequences are added to each well, such that all possible combinations of the identities of the first and second set of oligonucleotide sequences and their order of addition to the well are represented in the 16 wells.

7. The method according to claim 1, wherein the recognition sequence of the first and second set of oligonucleotide sequences consists of two bases and, prior to performing the first step, the nucleic acid population is sub-divided into 256 wells, each well containing oligonucleotides from the first set of sequences having one of the 16 possible recognition sequences, and wherein in the second reaction oligonucleotides from the second set of sequences are added to each well, such that all possible combinations of the identity of the first and second set of oligonucleotide sequences and their order of addition to the well are represented in the 256 wells.

8. The method according to claim 6, wherein the contents of each pair of wells to which the same pair of oligonucleotide sequences were added but in a different order, are combined to give 10 different wells.

9. The method according to claim 7, wherein the contents of each pair of wells to which the same pair of oligonucleotide sequences were added but in a different order, are combined to give 136 different wells.

10. The method according to claim 1, wherein each oligonucleotide sequence comprises a first sequence, a second sequence attached to the first sequence and a third sequence attached to the second sequence, in which the first sequence is complementary to the sequence of the primer portion of the adaptor, the second sequence is complementary to the known sticky end of the nucleic acids in the nucleic acid population, and the third sequence comprises the predetermined recognition sequence.

11. The method according to claim 10, wherein the recognition sequence consists of one base.

12. The method according to claim 10, wherein the recognition sequence consists of two or more bases.

13. The method according to claim 10, wherein in any one group of oligonucleotides having the same recognition sequence the third sequence consists of the recognition sequence and a pre-determined number of bases situated between the second sequence and the recognition sequence, all possible sequences of the predetermined number of bases in the third sequence being represented in that group of oligonucleotides.

14. The method according to claim 1, wherein the nucleic acid population is amplified by PCR prior to reaction with the oligonucleotide sequences.

15. The method according to claim 1, wherein the oligonucleotide sequences have equalized melting temperatures.

16. The method according to claim 15, wherein the melting temperatures are equalized by incorporating one or more analogues of natural nucleotides into the oligonucleotide sequences, the analogues comprising one or more modifications selected from the group consisting of base modifications, sugar modifications and backbone modifications.

17. The method according to claim 1, wherein the endonuclease is selected such that it cuts the nucleic acid at a site within the recognition site of the endonuclease.

* * * * *